United States Patent
Nazareth et al.

(10) Patent No.: US 11,447,767 B2
(45) Date of Patent: Sep. 20, 2022

(54) APPARATUS FOR AND METHODS OF THE DISRUPTION OF A BIOLOGICAL CELL

(75) Inventors: Nelson Nazareth, Upper Dean (GB); David Ward, Guisborough (GB); David Edge, Warlingham (GB)

(73) Assignee: BG RESEARCH LTD, Cambridgeshire (GB)

( * ) Notice: Subject to any disclaimer, the term of this patent is extended or adjusted under 35 U.S.C. 154(b) by 469 days.

(21) Appl. No.: 13/261,540

(22) PCT Filed: Jun. 15, 2011

(86) PCT No.: PCT/GB2011/000898
§ 371 (c)(1),
(2), (4) Date: Dec. 14, 2012

(87) PCT Pub. No.: WO2011/157989
PCT Pub. Date: Dec. 22, 2011

(65) Prior Publication Data
US 2013/0115670 A1   May 9, 2013

(30) Foreign Application Priority Data

Jun. 15, 2010 (GB) .................................... 1009998

(51) Int. Cl.
| | | |
|---|---|---|
| *C12N 15/10* | (2006.01) | |
| *B01L 7/00* | (2006.01) | |
| *C12N 1/06* | (2006.01) | |
| *F25B 21/04* | (2006.01) | |
| *C12N 1/08* | (2006.01) | |
| *B01L 3/00* | (2006.01) | |

(52) U.S. Cl.
CPC ............ *C12N 15/1003* (2013.01); *B01L 7/52* (2013.01); *C12N 1/066* (2013.01); *C12N 1/08* (2013.01); *F25B 21/04* (2013.01); *B01L 3/5029* (2013.01); *B01L 2200/027* (2013.01); *B01L 2200/04* (2013.01); *B01L 2200/10* (2013.01); *B01L 2200/141* (2013.01); *B01L 2200/147* (2013.01); *B01L 2300/044* (2013.01); *B01L 2400/049* (2013.01); *B01L 2400/0481* (2013.01); *B01L 2400/0487* (2013.01)

(58) Field of Classification Search
CPC ........... B01L 2200/027; B01L 2200/04; B01L 2200/10; B01L 2200/141; B01L 2200/147; B01L 2300/044; B01L 2400/0481; B01L 2400/0487; B01L 2400/049; B01L 3/5029; B01L 7/52; C12N 15/1003; C12N 1/066; C12N 1/08; F25B 21/04
See application file for complete search history.

(56) References Cited

U.S. PATENT DOCUMENTS

2006/0258012 A1* 11/2006 Yang et al.

OTHER PUBLICATIONS

Liu et al. Analytical Chemistry, ACS, vol. 76(7). Apr. 2004. pp. 1824-1831.*

* cited by examiner

*Primary Examiner* — Blaine Lankford
(74) *Attorney, Agent, or Firm* — Pabst Patent Group LLP

(57) ABSTRACT

Disrupting a biological cell includes freezing, boiling or perhaps alternately freezing and boiling material containing the biological cell using a thermoelectric cell with a working face, and a base face whereof is contiguous with a heat source/sink at a substantially constant temperature. Apparatus for the disruption process includes a peltier cell, a base face, which is flexibly attached to a heat source/sink held at a constant temperature, and a working face contiguous with a reaction vessel or holder thereof. Reversal of the voltage in the peltier cell enables the working face alternately to reach below freezing and above boiling temperatures, and/or with use of a resistive wire on the vessel or holder for heating, with the TEC used purely for cooling. The materials of the base face tend to inhibit disintegration of the peltier cell brought about by expansion and contraction by heat.

13 Claims, 2 Drawing Sheets

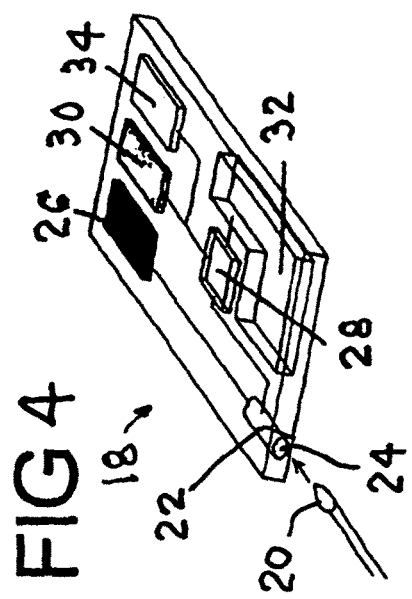
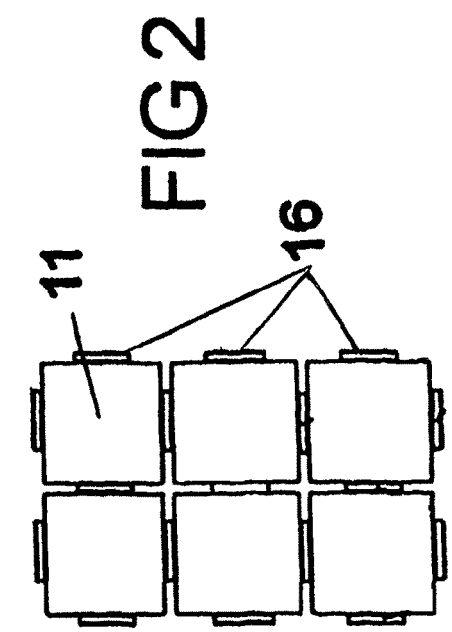
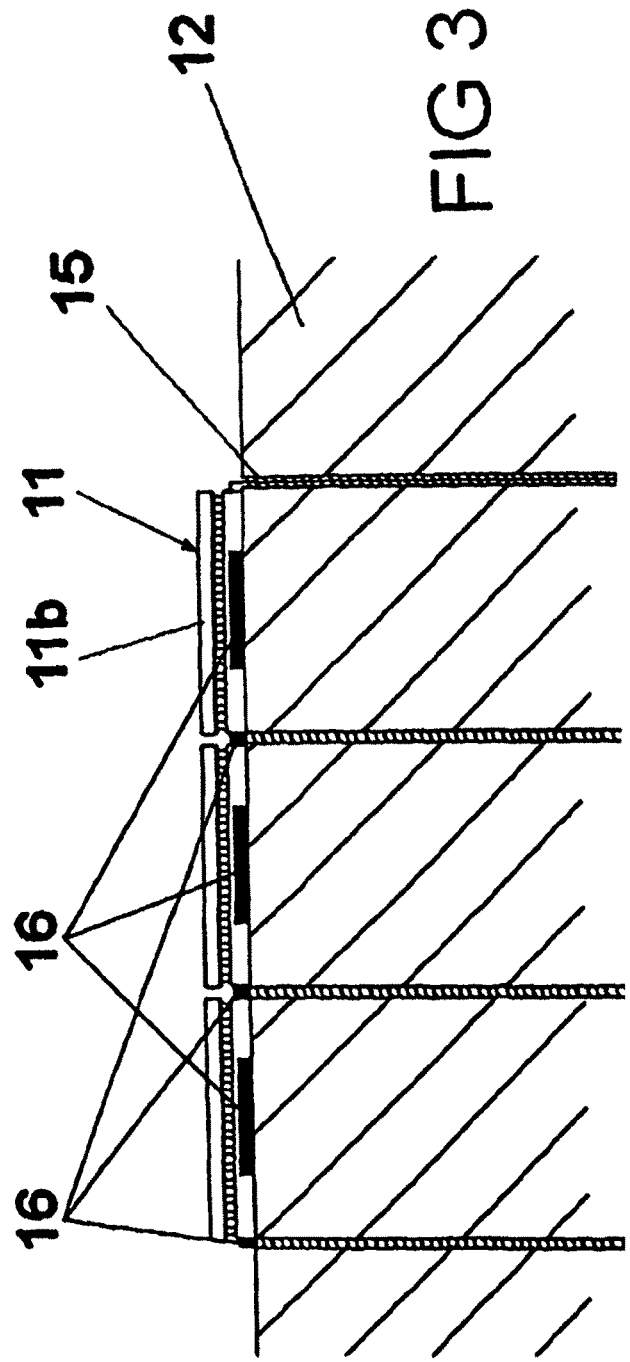

APPARATUS FOR AND METHODS OF THE DISRUPTION OF A BIOLOGICAL CELL

This is a US national stage application of International Application No. PCT/GB2011/000898, filed on Jun. 15, 2011, which, in turn, claims the benefit of UK application GB 1009998.4, filed on Jun. 15, 2010, both of which are incorporated herein by reference thereto.

FIELD OF INVENTION

The present invention relates to apparatus for and methods of the disruption of a biological cell. In particular, this invention relates to apparatus for and methods of the disruption of a biological cell to release the constituents of the cell by breaking the cellular membranes. This can be done in order to harvest one or more of the cell constituents for possible further processing in, for example, a biological reaction. Often it is the cellular nucleic acid (NA) component which is required for subsequent diagnostic analysis. NA hereinafter refers to both the RNA and DNA components. The process may be readily adapted to preferentially release the proteinaceous components of the cellular matrix if this be so required.

It is occasionally necessary to first purify the target NA molecules, in order to perform a biological reaction such as Polymerase Chain Reaction (PCR). For example NA is itself initially contained within a cell protected by a cellular membrane. Thus, in order to perform PCR on NA it is necessary to release the NA from its cell and into a carrier fluid suitable for downstream extraction and purification steps.

BACKGROUND

A number of methods are currently available for the disruption of cells. These include acid/base, enzymatic, sonication (disruption by ultrasonic waves) or mechanical separation. However, these are time consuming, some are overly damaging and disruptive to the NA itself, risk contamination and can give rise to irreproducible quality and quantities of the final purified NA produced. Moreover many of the existing techniques are not susceptible of automation.

DNA extraction is frequently performed in the presence of potentially dangerous chemicals such as phenol and guanidium salts in order to remove unwanted cellular components such as fats and proteins which may interfere with subsequent downstream processes. A rapid approach not reliant on these toxic additives would be desirable.

DNA extraction by temperature manipulation has been described in the literature. The use of boiling to physically disrupt the cellular membranes of the target cells releasing NA has been described. Likewise freezing by the use of liquid nitrogen has been particularly described in relation to plant material where the formation of ice crystals can physically disrupt the cellular membranes of these tissue types, they comprising polysaccharides.

This cellular lysis method would be suited for inclusion directly into a number of diagnostic assays. The process of amplifying nucleic acid sequences directly from simple targets such as human blood has been previously described. The cell types in these previous works are highly susceptible to lysis and as such no additional steps are required, save for optimisation of buffering protocols to minimise inhibition of the biological process by the cellular contents. Direct amplification of more complex targets, such as bacterial cells, has not been described and would require the addition of proteinases and long, time consuming downstream processing.

There are circumstances where it is highly desirable to obtain the release of NA in a very short time period, and at the same time to accurately control the quantity and quality of the purified NA. It would be valuable to be able to do this via manipulating a process that relies on simple time and temperature kinetics.

SUMMARY OF THE INVENTION

According to a first aspect of the present invention there is provided a process for the disruption of a cell comprising placing the material containing the cell in close proximity to a working face of a thermoelectric cell, the base face of which is in close proximity to a heat source/sink at a substantially constant temperature between the freezing and boiling temperatures of water, applying electric current to the thermoelectric cell to substantially change the temperature of the material.

The thermoelectric cell may be referred to, hereinafter, and interchangeably, as a Peltier cell, a Peltier, a peltier, or a TEC. The heat source/sink may be referred to, hereinafter, and interchangeably, as a heat sink, a Heat Removal Module, or a HRM.

In one embodiment the thermoelectric cell (TEC) is associated solely with a heat sink and there is provided a separate resistive heater element. In this embodiment the thermoelectric cell is therefore used solely to provide cooling hence reducing thermal stress on the TEC. The two independent heating and cooling means are advantageously controlled by the same electronic circuit so that any temperature set point can be reached. The preferred heater element may be a resistive heater wire in intimate contact with the vessel itself, for example comprising a coil of resistance wrapped round the thermally conductive vessel holder or an intermediate and thermally conductive holder such as a metal cup.

Heating means as set out in UK Patent Specification GB1100625.1 may alternatively be employed The process of the present invention can produce very rapid cell disruption, and is susceptible of manipulation by for example varying the number of cycles of thermal cycling performed, the buffering system utilised, if any, the target temperatures to be achieved and also the rate at which the ramping takes place.

In one embodiment the first step is to reduce the temperature at the working face thereof to freezing thus forming ice crystals in the target cells, and then causing the ice to thaw. In another embodiment the temperature is first raised to boiling, the sample then being allowed to cool. This latter embodiment is useful where the cell is relatively simple. Blood is an example of this. In yet another embodiment a thermal cycle is employed which may comprise alternately reversing the current to the thermoelectric cell, whereby the cell is more or less cyclically frozen and boiled. It will be appreciated that the temperature at which cell disruption takes place when the cell is boiling, is generally above 75° C.

A thermal cycle comprising freezing and boiling may be repeated a plurality of times. Rapid thermal cycling, perhaps even thermal shock, will also effect useful changes in the osmotic potential of the sample and thus assist in cell disruption. In certain circumstances the process may comprise several heating and cooling cycles without freezing, or with only occasional freezing, or equally several freezing and thawing cycles with only occasional or without heating.

The time span of a thermal cycle will depend on sample volume of sample and the vessel nature. Cycling speed may for example be related to ice crystal formation as different cooling speeds will create different sized ice crystals which will in turn affect cell disruption differently. The process may be individually optimised dependent on a number of factors such as the specific target organism from which the NA is being released, desired yield of NA required, size of individual NA fragments required and the physical requirements of any given downstream diagnostic assay being subsequently performed. This optimisation may take the form of altering temperatures, times, numbers of cycles and also the carrier medium itself into which the NA is released.

The process may however be employed to release other proteinaceous components of a cellular matrix if so required.

A cyclic process has a number of physical effects in the target cell. Firstly, heating the cell to boiling point causes cellular membranes to disrupt and therefore causes large scale release of cellular components into the extraction matrix. A process, in which heating, rather than cooling, is the first step, may be suitable for use on blood where the NA is surrounded by a simple lipid membrane. In this situation in fact, other than cooling the lysed material, no further cycling may be required after the first heating cycle. Heating alone is however insufficient to yield high quality NA from a number of organisms, since the NA remains associated with cellular proteins under these conditions. Subsequent freezing further disrupts the remaining cellular structures and repeating the freezing is sufficient to denature the proteins associated with the NA and hence render it suitable for purification and subsequent diagnostic use.

The extraction matrix, the fluid into which the NA is released, may also be such as to improve the outcome of the extraction process. In its simplest form any buffer known in the art, such as TRIS EDTA (trisaminomethane ethylenediamineetracetic acid), may be used to perform the freeze/thaw. Any extracted NA would be suitable for immediate downstream processing in this instance and as such this is the preferred embodiment. Some target cells may be resistant to the freeze/thaw extraction method and in these instances it may be necessary to include additional means to lyse the cellular contents. These may include inter alia initial enzymatic treatments, prior sonication and acid/base treatment. It is expected however that any additional disruption will be provided by manipulation of the cells' osmotic potential, for example by altering the salt concentrations and constituents of the extraction matrix and further by manipulation of the thermal cycling steps. Steps such as inclusion of enzymatic treatments, acid/base treatments, altering salt concentration and constituents of the extraction matrix may be effected prior to the process of the invention or may be incorporated in the apparatus and process.

The purification of a particular constituent from a thus disrupted cell may then be effected using processes which are known in the art, such as a simple alcohol based precipitation method or being passed through any of the commercially available "column" based systems. This will then render said NA suitable for subsequent biological process such as PCR.

In the preferred embodiment no such intermediate steps would be required and the released NA would be used in a downstream biological process, such as the Polymerase Chain Reaction (PCR), performed with enzyme and buffer mixtures optimised for this supernatant. In this instance PCR buffer would be the lysis medium, optimised for no loss of yield upon multiple freeze thaw cycles and additionally to be minimally inhibited by cellular contents. There are other documented approaches for such a direct method, but these are limited to samples that are very easily lysed, such as blood. The described invention will be able to amplify DNA directly from a much wider range of complex organisms by virtue of being able to disrupt protein and complex polysaccharide organelles via the freeze thaw methodology. This would bring the novel advantage of being able to be able to provide rapid PCR based diagnostics performed in a single closed tube vessel, without the need for multiple steps and therefore lend itself to non-expert operation.

A disruption process in accordance with the invention is readily susceptible to both automation and, more particularly, being effected as a closed process which may include a subsequent purification and PCR or other biological process. It is a feature of the invention to provide process and apparatus for the inclusion of a cellular lysis step as set out above directly into a downstream process such as PCR in order to further reduce the time and complexity of such processes. It is a particularly valuable feature of the invention that in most cases the process may be performed in a single vessel such as a tube, followed immediately, that is without intermediate purification, by PCR or other biological reaction.

Methods in accordance with this aspect of the invention provide a rapid and efficient lysis method, suitable for extracting plasmid and genomic DNA from a wide variety of organisms, such as for example, pathogenic bacteria and viruses. The disruption process of the present invention can be completed within the space of about one minute, certainly within five minutes and can be optimised to release any desired cellular component be this DNA, RNA or indeed desirable protein fractions.

When a voltage is applied to a TEC the current flow there through causes a first face thereof to become warmer and the second face to become cooler. Reversing the current causes the first face to cool and the second face to become heated. Thus a TEC can be used to perform both the heating and cooling of a sample containing the cells to be disrupted or lysed in a process in accordance with this invention, provided that a second or base face remains at a constant temperature intermediate boiling and freezing points whilst the first or working face is alternately at boiling and freezing temperatures. The TEC preferably has a voltage applied such that the sample is heated to the boiling point of water (100 degrees C.), at which point the voltage to the TEC is reversed and the sample is cooled to a temperature at or less than zero degrees C.

A problem however with using a TEC in this manner is that the coefficients of thermal expansion in the different materials used in the construction of a TEC, for example ceramic and metal will, in state of the art TECs, or just the fact of what can be termed a thermal fatigue where the working face continually expands and contracts laterally as a result of its temperature change whilst the base face substantially maintains its dimensions, result in delamination when such massive reversals of temperature are repeated.

This problem is addressed in a second aspect of the present invention.

According to this second aspect of the invention apparatus for carrying out the process of the present invention comprises a TEC having a base face and a working face separated by pillars, and a heat source/sink arranged to be held at a constant temperature, the base face being flexibly attached to the heat source/sink. In this manner the base face can expand and contract in contort with the working face while the latter expands and contracts due to temperature changes therein, but the propensity is reduced for detachment of the TEC from the heat source/sink or for disintegration of the TEC. The pillars are advantageously formed from bismuth telluride. In the context of microtitre equipment it may be important for the pillars to be as short as possible, in which case the electrical connections may best be formed of de-rated wire and the wire associated as closely as possible with the HRM (Heat Removal Module), for example arranged to pass therethough to keep the wire relatively cool.

Advantageously the base face is attached to a heat sink, hereinafter likely to be called a HRM and the working face to a reaction vessel, or more likely a reaction vessel holder in which, for example, the cell disruption of the present invention takes place. The attachment is preferably effected by a thermally conductive flexible adhesive. The adhesive may have a thermal conductivity greater than 1 W/mK, preferably exceeding 10 W/mK. Accordingly where the TEC has its faces metallised it is possible to use a solder to attach the base face to a heat sink, particularly when the heat sink itself is constructed of metal.

Preferably a soft solder, such as one based upon indium, is used and the thickness of the solder is made such as also to reduce sufficiently the thermal stress thereon and may be anything between tens of microns and a few millimetres. In order to ensure consistency in the thickness of the solder spacers may be emplaced into the solder. Such spacers will ensure that when the solder adhesive forms its liquidus phase the gap between the heat sink and TEC is controlled by this spacer.

An alternative process and apparatus is to employ a TEC merely for either heating or, more likely cooling, and to incorporate a separate heater or cooler as the case may be. This may avoid intolerable stresses in the TEC. In the case of heating a suitable structure may comprise a TEC having a hole therethrough to receive a vessel, the vessel also being surrounded by a heater. Normally such a structure will require different electrical supplies, one for the TEC and the other for the heater.

In this patent specification the word vessel refers to any device capable of holding a substance or a sample to be processed and a reaction vessel may accordingly comprise a well, a tube (open or closed) a slide, perhaps in the form of a silicon chip or a tray. The invention is particularly concerned with microtitre vessels in well form, though creating a TEC working face in the form of a vessel can be particularly advantageous.

In this invention the reaction vessels used to hold the cells to be lysed may be found individually or in either a linear, rectangular, circular array or other array. Typically the array will be such that it fits within the footprint of a standard microtitre plate, which is a format well known to those in the art. This format includes but is not limited to the following arrays:

3 by 2 reaction vessels, (6 reaction vessels)
6 by 4 reaction vessels, (12 reaction vessels)
12 by 8 reaction vessels, (96 reaction vessels)
24 by 16 reaction vessels and (384 reaction vessels)
48 by 32 reaction vessels (1536 reaction vessels)

According to an important feature of the invention there may be provided at least one Peltier per reaction vessel and the reaction vessel may be a microtitre vessel which may also be one in an array of such vessels, typically a 3×2 array or an integer multiple thereof.

The heat sink or FIRM may comprise a device as described in U.S. Pat. No. 8,597,937, which issued on Dec. 3, 2013, to David Ward et al., and which claims priority from PCT Patent Specification PCT/GB2007/003564, herein incorporated by reference. It may typically comprise a plate formed of such a metal as copper having therein a labyrinth of ducts associated with a liquid reservoir held at a constant temperature by appropriate fan means. The FIRM may accordingly form the base to an array of vessels, in which case it will be convenient to provide the HRM with location pins or crenellations.

BRIEF DESCRIPTION OF THE DRAWINGS

An embodiment of the invention will now be described by way of example with reference to the accompanying drawings, of which:

FIG. 2 is a plan view of the mounting of an array of TECs on a HRM;

FIG. 3 is a schematic diagram of the HRM.; and

FIG. 4 is a schematic diagram of a closed circuit device incorporating the invention.

DESCRIPTION OF THE PREFERRED EMBODIMENT

Figure 1:
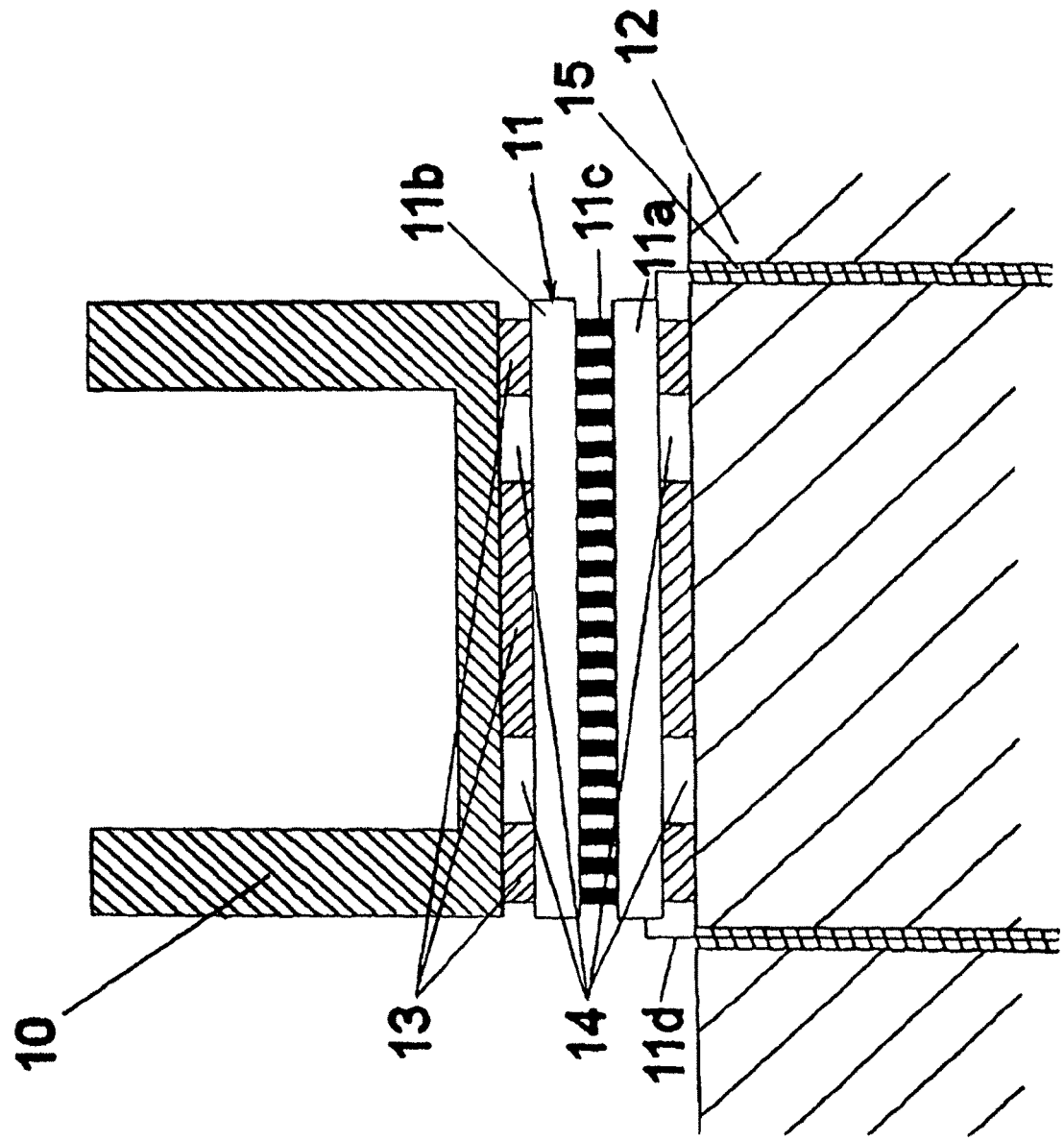
FIG. 1 is a schematic diagram of a vessel mounted on a HRM via a TEC.

FIG. 1 shows a reaction vessel 10 mounted via a peltier 11 to a HRM 12. The peltier 11 comprises a base plate 11a, a second plate 11b, a plurality of pillars 11c and feed wires 11d. The peltier 11 is attached both the vessel 10 and the HRM with an adhesive 13, the thickness of which is governed by spacers 14. The feed wires 11d pass through the HRM 12 from which they are electrically insulated by a thermally conductive plastics material 15.

As shown in FIG. 2 the HRM carries a plurality of crenellations 16 which form guides for the mounting of the peltiers 11. The HRM can alternatively posses a series of indentations such as in FIG. 3 into which the reaction vessels can be snugly mounted.

In use of the apparatus above described, with some target biological material in the vessel and the heat sink held at a temperature of the order of 50° C., current applied to the TEC in one direction reduces the temperature within the vessel to below freezing. This may in certain cases be sufficient to disrupt cells of the target material. The current may then be reversed so that the temperature in the vessel rises to above boiling. This cycle is repeated cyclically to complete disruption of the cells of the biological material. Thereafter PCR is employed to multiply a particular cell constituent for identification. A purification process may be performed intermediate the disruption and the undertaken to isolate the required cell constituent, normally its NA In the particular example shown the peltier 11 are 9 mm square and have bismuth telluride pillars 11c. The feed wires 11d are de-rated. An indium based solder 13 is used to attach the peltier 11 to the vessel 10 and the HRM 12.

In another embodiment the vessel 10 is not the reaction vessel as such but a holder therefore, arranged for snug reception of a microtitre reaction vessel. By this means the cost of disposable vessels can be kept low and standard such vessels used. An ideal microtitre reaction vessel for this situation is one having a high surface to volume ratio, with a base of the order of 7 mm×7 mm and a height of 3 to 5 mm, formed of a thermally conductive plastics material.

FIG. 3 illustrates the HRM block principle, whereby the TEC or heater and cooler elements (3) are attached to the block (1) by means of for example a soft, flexible indium solder. The fluid which can be water but preferably is a proprietary non electrically conductive medium such as 'Fluid XP' is flowed through the block via the inlet ports (2) in order to equalise temperatures across the block and hence make each element independent of each other and also to remove excess heat and allow the HRM to be maintained at the target temperature. The heater cooler elements are then thermally cycled around this pre-determined temperature in order to reduce the time and energy requirements for the freeze thaw process to take place.

FIG. 4 illustrates an envisaged embodiment of the NA extraction by heat/cool method, which permits NA extraction, purification and subsequent amplification and to occur in a self contained cartridge 18 or "biochip". The advantage of this embodiment is that the entire process can be performed in a closed tube environment, minimizing the likelihood of contamination and bringing commensurate saving in time and expense as all steps can be performed on a single instrument and consumable. The process involved is highlighted below;

1. The operator inserts a sample, for example on a swab 20 taken from a patient suspected of suffering from a particular disease, through an orifice 24 which is liquid tight once the swab has been inserted, ideally by means of application of a sealant film to form a sealed compartment 22. The system may be adapted for the use of many differing starting materials e.g. use of a syringe through a luer lock fitting or 'solid' material through a funnel type orifice with appropriate sealing for system pressure.
2. The sealed compartment 22 containing the sample is then flooded with buffer from a fluid chamber 26 by means of positive displacement into the a reaction station chamber 28, in so doing the sample containing suspected pathogen cells is transferred as a liquid into the reaction chamber.
3. Lysis of the pathogen cells and subsequent release of NA is mediated by repeated thermal cycling of the reaction chamber 28 as previously described in this application, to assist in the lysing process of the constituents of the fluid contained in chamber 26 may be altered dependent on the target pathogen and specific assay to be performed.
4. In a particular embodiment the buffer fluid contained in chamber 26 can contain magnetic beads specific to the target pathogen cell, binding either by antibody mediated means or by direct oligonucleotide hybridisation as known in the art. The requirement for this step is dependent on the need to either preferentially capture a target NA in preference to total NA or to ensure that every possible pathogen NA molecule is isolated as a means to increase sensitivity of subsequent analyses.
5. A magnetic field may be applied to the reaction chamber 28 in the instance of using magnetic bead for capture, binding the beads which have the target NA bound to them. The cellular waste resulting from the freeze/thaw is then rinsed repeatedly by fluid contained in a chamber 30. The waste from the process is flushed into a chamber 32 so that the whole process is self contained.
6. The final step is to release the bound nucleic acid from the magnetic beads by means of gentle warming and resuspension in the amplification buffers contained in a chamber 34. Where magnetic separation is not required a proportion of the total cellular NA in the liquid phase is discarded to waste, leaving only the amount required to be combined with the amplification components supplied by the chamber 34. The contents of chamber 34 may constitute the reagents necessary for a number of biological amplification protocols, in order to detect small initial numbers of target molecules. In the preferred embodiment this would be real-time PCR including the addition of fluorescently labelled primer molecules sequence specific for the pathogens of interest.

The fluid chambers may be activated by a number of means:

Positive displacement, wherein the fluid chamber 26 is compressed, squeezing the fluid into the reaction chamber 28. This method also includes the benefit in that fluid can be moved bi-directionally if required for rinsing or mixing steps and requires less volume to store waste fluid.

Positive pressure. In this way air is injected into the fluid chamber 26 through a seal. This seal is punctured by a needle (not shown) upon cartridge insertion and when required air pushes the fluid out of the chambers. The seal should be designed such that it self-seals when the cartridge 18 is removed from the instrument.

Negative pressure may also be used.

The nature of the design allows the benefit of subsequently utilizing the TEC that controls the freeze/thaw process to perform any thermal cycling process, such as the PCR process in the preferred embodiment.

In general, the above-identified embodiments are not to be construed as limiting the breadth of the present invention. Modifications, and other alternative constructions, will be apparent which are within the spirit and scope of the invention as defined in the appended claims.

The invention claimed is:

1. A closed tube process of amplifying a target nucleic acid and comprising:
   i. placing a sample suspected of containing a biological cell or virus comprising the target nucleic acid material in a microtitre reaction vessel (10) together with real time PCR fluorescently labeled primer molecules sequence specific for the target of interest, and closing the vessel 10;
   ii. placing the reaction vessel (10) in a holder, the holder being adapted to receive the microtitre reaction vessel (10) snugly and having attached thereto the working face (11b) of a thermoelectric cell (11), the base face (11a) of which is flexibly attached to a heat source/sink block (12) through which fluid flows at a substantially constant temperature between the freezing and boiling temperatures of water, the base face (11a) and the working face (11b) being separated by pillars (11c);
   iii. applying an electric current to the thermoelectric cell (11) first freezing, thus to form ice crystals in the biological cell or virus in the sample, then reversing the current and thawing said ice crystals;
   iv. repeating step iii until lysis of the biological cell or virus has occurred;
   v. carrying out real time PCR on the released nucleic acid in the same closed vessel 10.

2. A process as claimed in claim 1 and comprising boiling the vessel contents after freezing the contents.

3. A process as claimed in claim 2, and wherein the boiling comprises subjecting the material to a temperature of at least 75° C.

4. A process as claimed in claim 1, and wherein the freezing step is preceded by any one of initial enzymatic, prior sonification, and acid/base, treatments.

5. A process as claimed in claim 4 and wherein the reaction vessel (10) is formed of a thermally conductive plastics material.

6. A process as claimed in claim 5 and wherein the attachment is effected with a thermally conductive flexible adhesive having a thermal conductivity greater than 1 W/mk.

7. A process as claimed in claim 6 and wherein the adhesive has a thermal conductivity greater than 10 W/mK.

8. A process as claimed in claim 6 and wherein the adhesive comprises a soft solder.

9. A process as claimed in claim 1 and wherein the heat source/sink block (12) comprises a metal having therein a labyrinth of ducts associated with a liquid reservoir arranged for being held at a constant temperature.

10. A process as claimed in claim 1 and wherein the thermoelectric cell has connecting wires which pass through the heat source/sink block.

11. A process as claimed in claim 1 and wherein the eat source/sink block (12) forms the base to an array of reaction vessel holders.

12. A process as claimed in claim 9 and wherein the thermoelectric cell is less than 10 mm square.

13. A process as claimed in claim 1 and wherein the heat source/sink block (12) is provided with crenellations (16).

* * * * *